United States Patent [19]

Freedenthal et al.

[11] Patent Number: 4,505,734

[45] Date of Patent: Mar. 19, 1985

[54] COPPER BASED ALGAECIDES AND AQUATIC HERBICIDES

[75] Inventors: Carol B. Freedenthal; Marion D. Meyers; Graham A. Stoner, all of Houston, Tex.

[73] Assignee: Kocide Chemical Corporation, Houston, Tex.

[21] Appl. No.: 521,636

[22] Filed: Aug. 9, 1983

Related U.S. Application Data

[63] Continuation of Ser. No. 323,307, Nov. 20, 1981, abandoned, which is a continuation of Ser. No. 162,379, Jun. 23, 1980, abandoned, which is a continuation of Ser. No. 744,299, Nov. 23, 1976, abandoned, which is a continuation of Ser. No. 579,805, May 22, 1975, abandoned, which is a continuation of Ser. No. 397,136, Sep. 13, 1973, abandoned.

[51] Int. Cl.$^3$ .............................................. A01N 33/04
[52] U.S. Cl. ............................................ 71/67; 71/66; 71/97
[58] Field of Search ....................................... 71/67, 66

[56] References Cited

U.S. PATENT DOCUMENTS

| | | | |
|---|---|---|---|
| 2,446,682 | 8/1948 | Whitner | 71/97 |
| 2,734,028 | 2/1956 | Domogalla | 71/67 |
| 3,463,628 | 8/1969 | Hyde | 71/66 |
| 3,634,061 | 1/1972 | Geiger et al. | 71/66 |
| 3,716,351 | 2/1973 | Kunkel et al. | 71/67 |
| 3,844,760 | 10/1974 | Nelson | 71/67 |
| 3,905,797 | 9/1975 | Kunkel et al. | 71/67 |
| 4,324,578 | 4/1982 | Seymour et al. | 71/67 |

Primary Examiner—Glennon H. Hollrah
Assistant Examiner—R. Covington
Attorney, Agent, or Firm—Kenneth H. Johnson

[57] ABSTRACT

Basic copper salts such as cupric hydroxide, basic copper chloride, basic copper sulfate and the like with an alkanolamine result in an unexpectedly beneficial composition useful in a method for treating bodies of water to arrest or eliminate the growth of algae and aquatic weeds; a more stable and less corrosive solution is obtained for storage purposes when the insoluble basic copper salts are reacted with an alkanolamine such as trialkanolamine or mixtures or tri- and dialkanolamines to produce a water soluble copper complex of the organic compounds; moreover, the formed complex of the insoluble basic salts provides a higher copper content in the solution formed by the complex when compared to the acid, water soluble copper salts; full effectiveness of the complex has been observed for extended period of time without decrease of soluble copper content.

14 Claims, No Drawings

COPPER BASED ALGAECIDES AND AQUATIC HERBICIDES

This application is a continuation of Ser. No. 323,307 filed Nov. 20, 1981, now abandoned, which in turn is a continuation of Ser. No. 162,379, filed June 23, 1980, now abandoned, which in turn is a continuation of Ser. No. 744,299, filed Nov. 23, 1976, now abandoned, which in turn is a continuation of Ser. No. 579,805, filed May 22, 1975, now abandoned, which in turn is a continuation of Ser. No. 397,136, filed Sept. 13, 1973, now abandoned.

This invention relates to a stable algaecide and aquatic weed herbicide composition and more particularly, to a storage stable algaecide and aquatic weed herbicide composition of basic copper salts as a complex with an alkanolamine, prepared from a basic copper salt and an alkanolamine whereby said copper complex is formed.

BACKGROUND OF THE INVENTION

Numerous bodies of water such as rivers, lakes, ponds, streams, brooks, drinking water supplies, irrigation systems, agricultural water systems, aquariums, fountains or ornamental water systems, fish ponds, swimming pools, shower rooms and industrial water systems, such as cooling towers and ponds, frequently have an excessive growth of algae and other microorganisms, which impart an unacceptable quality to the body of water. Moreover, some of the enumerated bodies of water develop excessive aquatic weed growth, which interferes with the flow of water and renders the body of water unsuitable for the intended use or diminishes the economic value of it. Weeds and algae in the recited bodies of water are controlled by various means, including chemical algaestats, algaecides, and herbicides.

THE PRIOR ART

For the control of the algae, the prior art has used, with considerable success, acid or water soluble salts of copper such as inorganic or organic salts, e.g., copper sulfates, chlorides, bromides, acetates, nitrates, citrates, gluconates and alkanolamine complexes of said acids or water soluble salts or the like. The acid copper salts are disclosed in U.S. Pat. No. 2,734,028 and are used in the form of a complexes with an alkanolamine; the acid salts of copper compounds reacted with aliphatic hydroxy acids are disclosed in U.S. Pat. No. 2,400,863.

However, the stability of the copper salt or its complex, such as mentioned above, has left much to be desired and further improvements have been shown in U.S. Pat. No. 3,716,351, which patent discloses an algaecide composition containing a complex of a water soluble copper salt with an alkanolamine and stabilizers therefor. Additionally, cobalt salts with an alkanolamine have also been disclosed. For stabilizing the copper salts against decomposition to elemental copper and/or cuprous oxide in storage in the last mentioned patent it has been taught that an effective amount of an acetylenic diol and an alkali metal halogenate prevents the copper alkanolamine complex from decomposition. In U.S. Pat. No. 3,716,351 it has been mentioned specifically that the additives are for preventing the decomposition of the copper complex and precipitation of insoluble copper or cuprous oxide during storage.

Further, in U.S. Pat. No. 2,734,028 it has been mentioned that in alkaline waters with a pH over 7 (and particularly in waters containing carbonates or bicarbonates), copper sulfate is generally ineffective due to the waste caused by precipitation of copper in the form of either insoluble copper hydroxide or copper carbonate.

BRIEF DESCRIPTION OF THE INVENTION

It has now been found that, contrary to the prior art teaching about the preparation of the copper alkanolamine complex using water soluble acid copper salts, the use of water insoluble, basic copper salts such as cupric hydroxide, basic copper chloride, basic copper sulfate and the like, result in an unexpectedly beneficial composition for a method of treating the enumerated bodies of water to arrest or eliminate the growth of algae and aquatic weeds and providing a more stable and less corrosive composition for storage purposes when the insoluble basic copper salts are reacted with an alkanolamine such as trialkanolamine or mixtures or tri-and dialkanolamines to produce a water soluble copper complex of the organic compound. As mentioned before, the improved storage stability of the disclosed complex is also noteworthy. Moreover, the formed complex of the insoluble basic salts provides a higher copper content in solution when compared to the acid, water soluble copper salts. Whereas the materials made by the previous art show a decrease in soluble copper content and thus lose effectiveness for the intended purposes, full effectiveness of the novel complex has been observed for extended period of time.

Still further, it has been found that the basic copper alkanolamine complex possesses herbicidal properties such as controlling aquatic weeds of the type Hydrilla verticillata, Maiad, Milfeil and the like.

DISCUSSION OF THE INVENTION

As an alkanolamine useful in the present formulation of the copper complex compositions, alkanolamines having from 1 to 10 carbon atoms in the alkyl group are employed. These alkanolamines consist of monoethanolamine, diethanolamines, triethanolamines, dimethyl ethanolamine, diethyl ethanolamine, amino ethylethanolamine, monoisopropanolamine, diisopropanolamine, triisopropanolamine, methyldiethanolamine, and the like. The preferred compound is triethanolamine and the preferred combination of it is an 85% mixture of triethanolamine containing 15% of diethanolamine with the respective basic copper salt. An aqueous formulation for the basic copper salt complex with the alkanolamine can range up to 10% of copper based on the total amount of the copper salt and the amine; it has been found that an aqueous formulation of 8% copper as the triethanol amine complex in a ratio of 2:1 triethanolamine to copper is very acceptable.

Of the basic copper salts, copper hydroxides and related species have been found to be most advantageous, e.g., cupric hydroxide, copper hydroxide, copper hydrate. The copper-alkanol amine complex is prepared by dissolving copper hydroxide or hydrated oxide in an aqueous solution of the alkanolamine being selected. In the event of a less pure copper hydroxide starting material, careful filtration by means of filtering aids and the like, allows the removal of turbidity causing agents to yield a clear, blue solution. A method for reacting triethanol amine with copper hydroxide or hydrated oxide which has made in situ by reacting copper sulfate and base and forming a solution containing less than one percent copper is disclosed in U.S. Pat. No. 2,446,682. However, a reaction with of an insoluble basic copper salt and an alkanolamine, preferably triethanolamine, is unknown for obtaining a solution containing more than one percent of copper. Moreover, a solution containing up to 10 percent of copper as described herein has now been discovered. The use of the above-described complexes such as in U.S. Pat. No. 2,446,682 for controlling algae as well as using these as aquatic weed herbicides has heretofore not been known.

EXAMPLE 1

For purposes of illustration, the herein disclosed complexes were prepared by admixing triethanolamine with water at a temperature of about 38° C. using about 1500 pounds of triethanolamine (85% triethanolamine-TEA, 15% diethanolamine-DEA) and 84 gallons of water and adding thereto 500 pounds of cupric hydroxide of a copper content of 54.5% copper and reacting the complex for two hours at a maximum temperature of 58° C. Thereafter, after about two hours an additional 81 gallons of water were added. The copper content of the solution was about 8.10% before filtering the solution. After filtering the solution and cooling, the copper content was found to be 7.99% and the density of the solution at 25° C. was 1.202. In a similar manner, solutions were made up which contained 8.1% of copper before filtering and 8.05% of copper after filtering. Another solution containing 8.12% of copper before filtering and having a density of 1.204 was obtained.

If filtration is needed, it can be achieved by adding a filtering aid of conventional properties such as High-Flow Super Cell, 2% on basis of solution and filtering by a centrifuge or leaf filter.

EXAMPLE 2

Three hundred forty-five gallons of the copper hydroxide triethanolamine complex were prepared in the following manner. To 1520 pounds of stirred commercial grade triethanolamine-85 (defined in Example 1) were added: 1) 84 gallons of water; 2) 23 pounds of 93% sulfuric acid (for pH adjustment) in five gallons of water; and 3) 442 pounds of copper hydrate (relatively pure copper hydroxide containing no phosphate and only trace amounts of sulfate) containing 62.6% copper (mole ratio TEA:Cu=2:1). After stirring for one hour, the temperature of the solution was 55° C. and all the copper hydrate had dissolved. Eighty-six gallons of water was added to the solution and stirring was continued for 15 minutes.

After cooling to 25° C., the dark blue product showed the following properties: 8.06% Cu, 1.195 specific gravity, 9.8 pH, and 45 cps viscosity. After a period of 15 weeks at room temperature, there was no visible deposit or precipitation in the storage containers and the solution remained clear.

EXAMPLE 3

To a solution of 298 g. triethanolamine-99 (99% TEA, 1% DEA) in 190 ml water was added 117 g. basic copper sulfate ($3Cu(OH)_2 \cdot CuSO_4$, 54.3% copper). The mixture was stirred for two and one-half hours at a maximum temperature of 35° C. After this period all the basic copper sulfate had dissolved and an additional 190 ml of water was added; stirring was continued for 15 minutes. At 25° C. the solution had a copper content of 7.8%, a pH of 8.70 and specific gravity 1.22.

EXAMPLE 4

To a solution made from 301 g. triethanolamine-99 and 190 ml of water was added 110 g. technical grade copper oxychloride, $3Cu(OH)_2 \cdot CuCl_2$, 58% Cu. The mixture was stirred at 65° C. for four hours. After this period 190 ml of water were added; the mixture was stirred another 15 minutes. The undissolved solid was removed by filtration. The filtrate was a clear blueish-green solution, 8.01% copper, pH 8.4, and specific gravity 1.204 at 25° C.

EXAMPLE 5

To a solution made from 301 g. triethanolamine-99 and 186 ml of water was added 120 g. basic copper carbonate, 53% Cu. The mixture was stirred at 70° for five hours. After this period 180 ml of water were added and stirring was continued 15 minutes. The undissolved solid was removed by filtration yielding a clear dark blue solution. The solution was 7.08% copper, pH 9.4, and specific gravity 1.17 at 25° C.

OTHER EMBODIMENTS

When using copper hydrate, cupric hydroxide, basic copper carbonate, basic copper sulfate, and copper oxy-chloride, a reaction occurs between the basic copper material and the alkanolamine when these are mixed in water and in all cases the reaction product is a blue solution. The complex produced from the copper hydroxide contains 1 mol of the alkanolamine per mol of copper with one or more associated hydroxide ions. The copper hydroxide-alkanolamine complex can be precipitated from the solution by the addition of twice the volume of an organic solvent such as acetone. The insoluble copper hydroxide-alkanolamine precipitate can be easily filtered and dried. The dark blue crystals are very soluble in water and in lower alcohols, i.e., alcohols having from 1 to 6 carbon atoms and these can be sold as concentrates.

These concentrates can easily be reconstituted in to useful solutions and these solutions have the same physical and chemical properties as the original solution.

Upon heating the dark blue crystals at 110° C., two mols of water are driven off yielding a greenish hygroscopic solid. This solid, when dissolved in water gives a green solution which slowly rehydrolyzes to become blue on standing and the final solution has the same physical and chemical properties as the original solution, hence the drying of the crystals does not affect the properties.

It is postulated that the blue species is a dimer of the complex. Although mono and diethanolamine complexes are formed, the preferred triethanolamine complexes are the desired complexes because these do not hydrolyze as readily when diluted with water. However, the above indicated mixture of 85% triethanolamine and 15% diethanolamine forms the most advantageous combination of the complex.

Generally, a ratio of about 1.3:1 of the triethanolamine to copper gives a solution of 10% copper; the solubility is reduced with increasing amounts of triethanolamine.

It has been found that the solution of cupric hydroxide, and triethanolamine containing 8% and 9% copper in a ratio of 2 triethanolamine to 1 copper and 1.5 triethanolamine to 1 copper, respectively, in a solution form were stable up to a pH of 12 and 11, respectively. Hence, it can be fairly concluded that the solutions are stable at a pH from 10 to 11 at a triethanolamine to copper ratio of 2:1 or greater while the copper concentration is in a range from 7% to 8%.

UTILITY OF THE INVENTION

An aqueous solution of triethanolamine-basic copper complex may be employed by introducing the solution in any of the desired bodies of water in amounts from 0.1 ppm up to 10 ppm (ppm-parts per million) expressed as elemental copper. Generally, from 0.2 ppm to 1.0 ppm is employed, (2.5 ppm to 12.5 ppm on basis of the complex); a range from 0.1 ppm to 6 ppm is a practical, broad range when expressed as elemental copper. The parts per million (ppm) refer to elemental copper, which for a 8% copper containing complex solutions would be from 1.25 to 75 ppm of copper-triethanolamine complex formulated solution.

It has also been found that the toxicity of the herein disclosed algaecidal and herbicidal composition favorably compares with any of the existing algaecides and herbicides based on copper complexes. For example, when testing for mortality, expressed as a percent mortality of blue gill sunfish, from 0.5 ppm to 1.5 ppm (elemental copper) of the copper hydroxide-85% triethanolamine, 15% diethanolamine complex, after an exposure of 8 to 96 hours, no mortality was observed. After increasing the amount to 2.0 ppm (elemental copper) 30% mortality was observed after 96 hours. The mortality rate of blue gill sunfish compares very favorably with the 100% mortality observed for 2.0 ppm (elemental copper) when using the conventional water soluble inorganic acid copper salt triethanolamine complexes.

The algaecidal compositions, as mentioned above, may be sold in the form of the blue crystal, or in a properly diluted water solution.

The corrosiveness of the solution form of the algaecide composition was determined according the following method. Coupons of steel, brass, aluminum, polyethylene and stainless steel (316) were immersed for a total of 29 days (17 for stainless steel) and the weight increase measured in a solution having a copper content of 7.3% (elemental copper). The increase in weight was compared with coupons in a the solution based on a commercial product (Cutrine-which apparently is the solution disclosed in U.S. Pat. No. 2,734,028) having a copper content of 7.4% (elemental copper). The increase in weight of the prior art product was most pronounced on aluminum coupons (encrusted with copper) whereas the present composition showed tolerable increases (1.50 gram coupon gained from 0.2204 gram to as low as 0.0588 gram.) Another illustration about corrosiveness caused by dilute solutions is given in the Table below.

TABLE

COMPARISON OF CORROSION DATA FOR BASIC CU COMPLEX AND CUTRINE IN DILUTE SOLUTIONS

| Solution | Exposure Time | Wt. Loss as % of tot. Coupon Wt. | Coupon Appearance |
|---|---|---|---|
| | | Type 6061 Aluminum | |
| K-LOX Basic Cu Complex* 0.8% | 2 hrs. | 0.15% | Very slightly drknd. |
| | 4 hrs. | 0.08% | Very slightly drknd. |
| | 8 hrs. | 0.11% | Very small pits ntd. |
| | 24 hrs. | 0.14% | Very small pits ntd. |
| CUTRINE**, 0.8% Cu | 2 hrs. | 2.77% | Pits over 10% of srfce. |
| | 4 hrs. | 8.25% | Pits |
| | 8 hrs. | 21.20% | Lge. pits and ragged edg |
| | 24 hrs. | 87.8% | Almst complete disintegration. |
| | | Mild Steel | |
| K-LOX Basic Cu Complex* 0.8% Cu | 2 hrs. | 0.08% | Discolored surface |
| | 4 hrs. | 0.08% | Discolored, slightly rsty. |
| | 8 hrs. | 0.09% | Discolored, slightly rsty. |
| | 24 hrs. | 0.10% | Discolored, slightly rsty. |
| CUTRINE**, 0.8% Cu | 2 hrs. | 0.13% | Brownish coating. |
| | 4 hrs. | 0.23% | Brownish coating. |
| | 8 hrs. | 0.58% | Surface rough, brwnsh deposits. |
| | 24 hrs. | 2.03% | Heavy drk brwn. layer, shallow pts; copper deposits |

*Copper hydroxide-triethanolamine complex
**Defined above

However, results with brass, stainless steel, and polyethlene were comparable. As can be appreciated, lower corrosiveness is highly desirable because of longer life imparted to pumps, fittings, aluminum pipe in spraying and irrigation systems as well as any metallic items which may be in the bodies of water treated.

Because of greater stability and tolerance to higher pH values, the presently disclosed copper complexes are useful in irrigation systems in the Western United States because alkaline water is encountered in these systems.

As mentioned before, the range of pH conditions within which the disclosed complexes are useful, which is found for most common bodies of water, is between 7.0 to 12.00. Moreover, the complex functions over a broad range of pH values. For a 8.0% solution, no stabilizing agents are required to maintain the 8.0% copper content in solution during storage at ambient (about 20° C. ±10°) to 40° C., temperature.

The algaecidal composition is effective against all common forms of algae, including filamentous algae, such as Cladaphora and Spirogyra, planktonic algae such as Microcystis and Anabaena, branched algae such as Chara vulgaris and Nitella, swimming pool algae, commonly referred to as black, brown, and red algae, and algae found in ponds such as Dictyosphaerium, Spirogyra, Oedogonium, Chlorococcum, Pithophora, Hydrodictyon, and Lyngbya.

What is claimed is:

1. A water soluble aqueous concentrate comprising a water solution of a complex of copper hydroxide and a trialkanolamine or mixture of a trialkanolamine and a dialkanolamine containing a major proportion of trialkanolamine, such alkanolamines having 2 to 6 carbon atoms in the alkanol moieties, the ratio of alkanolamine to copper hydroxide being in the range of from 1:1 to 3:1, said solution containing from 7 to 10 percent copper expressed as elemental copper, and wherein the pH is from 8.7 to 9.8.

2. A water soluble aqueous concentrate in accordance with claim 1 comprising a complex of copper hydroxide and a trialkanolamine or mixture of a trialkanolamine with no more than 15 percent dialkanolamine.

3. A concentrate of claim 1 wherein the copper content is from 7.8 to 10 percent.

4. A concentrate of claim 1 wherein the pH is from 9.4 to 9.8.

5. A concentrate of claim 1 wherein the copper content is 8 to 10 percent.

6. A concentrate of claim 3 in which the alkanolamine is triethanolamine or a mixture of 85 percent triethanolamine and 15 percent diethanolamine.

7. A concentrate of claim 3 in which the alkanolamine is a mixture of 85 percent triethanolamine and 15 percent diethanolamine.

8. A concentrate of claim 7 in which sulfuric acid is included for pH adjustment.

9. A concentrate of claim 2 wherein the copper content is from 7.8 to 10 percent.

10. A concentrate of claim 2 wherein the pH is from 9.4 to 9.8.

11. A concentrate of claim 2 wherein the copper content is 8 to 10 percent.

12. A concentrate of claim 9 in which the alkanolamine is triethanolamine or a mixture of 85 percent triethanolamine and 15 diethanolamine.

13. A concentrate of claim 9 in which the alkanolamine is a mixture of 85 percent triethanoalmine and 15 percent diethanolamine.

14. A concentrate of claim 13 in which sulfuric acid is included.

* * * * *